(12) United States Patent
Musa

(10) Patent No.: US 7,428,849 B2
(45) Date of Patent: Sep. 30, 2008

(54) SAMPLE COLLECTION ARRANGEMENT OPERATIVE IN ENVIRONMENTS OF RESTRICTED ACCESS

(76) Inventor: Christine P. Musa, 26 Parker St., Belvidere, NJ (US) 07823

( * ) Notice: Subject to any disclaimer, the term of this patent is extended or adjusted under 35 U.S.C. 154(b) by 563 days.

(21) Appl. No.: 11/040,413

(22) Filed: Jan. 21, 2005

(65) Prior Publication Data

US 2008/0000146 A1      Jan. 3, 2008

Related U.S. Application Data

(63) Continuation of application No. 10/379,348, filed on Mar. 4, 2003, now abandoned.

(60) Provisional application No. 60/361,802, filed on Mar. 5, 2002.

(51) Int. Cl.
*G01N 1/12* (2006.01)

(52) U.S. Cl. .................................... 73/864.51

(58) Field of Classification Search ............... 73/864, 73/864.51, 864.63
See application file for complete search history.

(56) References Cited

U.S. PATENT DOCUMENTS 4,061,038 A * 12/1977 Clarke, Jr. ............... 73/864.51
4,157,664 A * 6/1979 Robinson ................. 73/864.64
4,454,775 A * 6/1984 Ellis ........................ 73/864.51
4,563,896 A * 1/1986 Arnold .................... 73/864.51
5,202,094 A * 4/1993 Jones et al. ................. 422/102
5,442,970 A * 8/1995 Hutchins ................. 73/864.63
5,444,934 A * 8/1995 LaTouche ............. 43/18.1 CT
5,454,275 A * 10/1995 Kabis ...................... 73/864.51
5,601,324 A * 2/1997 Purcell ...................... 294/31.2
5,739,439 A * 4/1998 Gruidel et al. ........... 73/864.51
7,014,231 B1 * 3/2006 Callen ......................... 73/427

FOREIGN PATENT DOCUMENTS

JP          63061778 A    *   3/1988

* cited by examiner

*Primary Examiner*—Hezron E. Williams
*Assistant Examiner*—Nashmiya S Fayyaz
(74) *Attorney, Agent, or Firm*—Mark L Hopkins, Esq.

(57) ABSTRACT

A sample collection arrangement for obtaining organism-populated water samples from locations in the environment that are highly restricted in terms of physical access, which comprises a telescopic pole and one or more containers each of which, together with the pole, is designed to accommodate the physical restrictions encountered in sampling, such as severely grated storm drains, and a coupling arrangement demountably coupling the container and the pole that enables the container to be flexibly oriented in relation to the water source through virtually any acute angle relative to the pole's longitudinal dimension. Multiple embodiments of the container and coupling arrangement, as a well as a security component with extension capability, are disclosed.

17 Claims, 9 Drawing Sheets

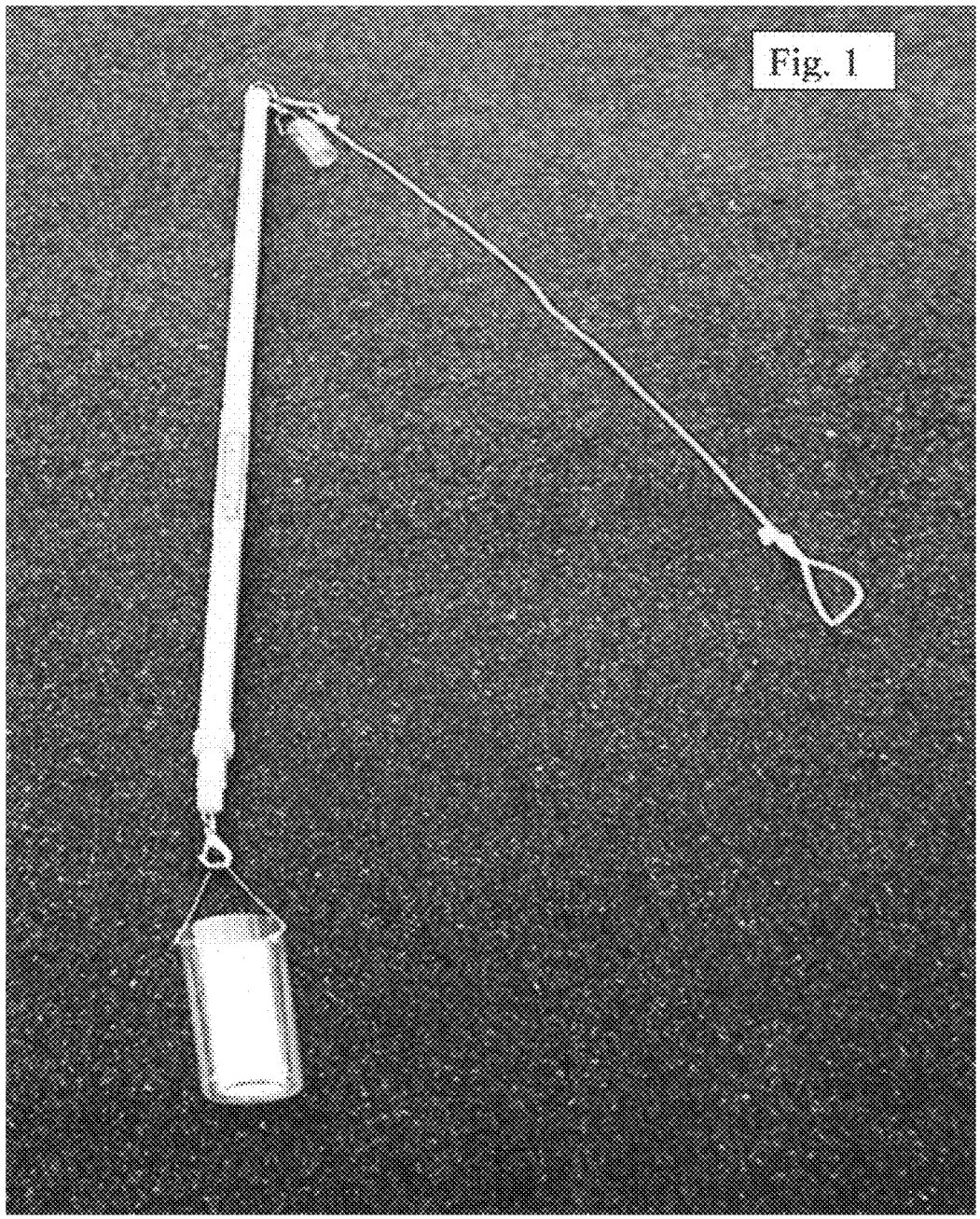

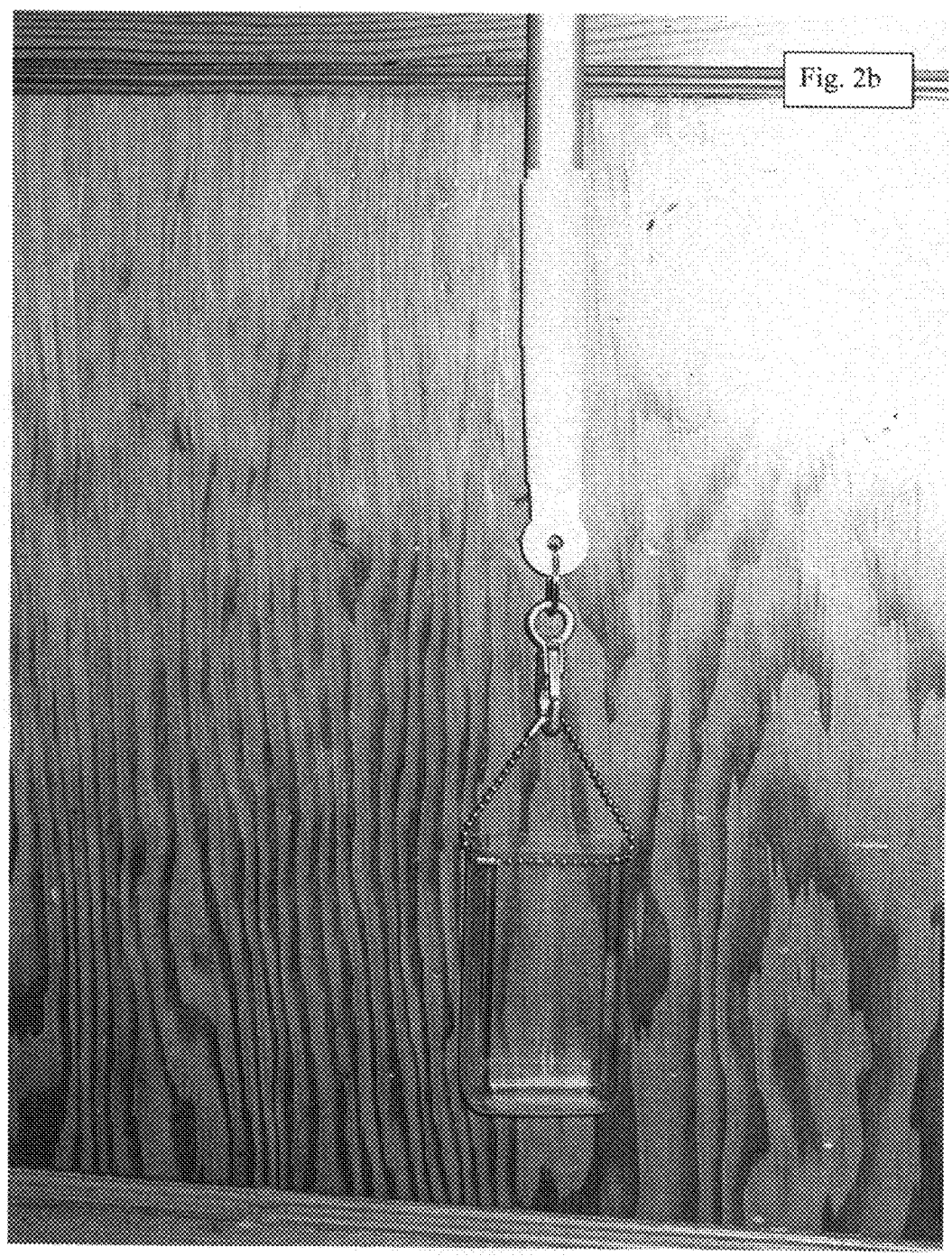

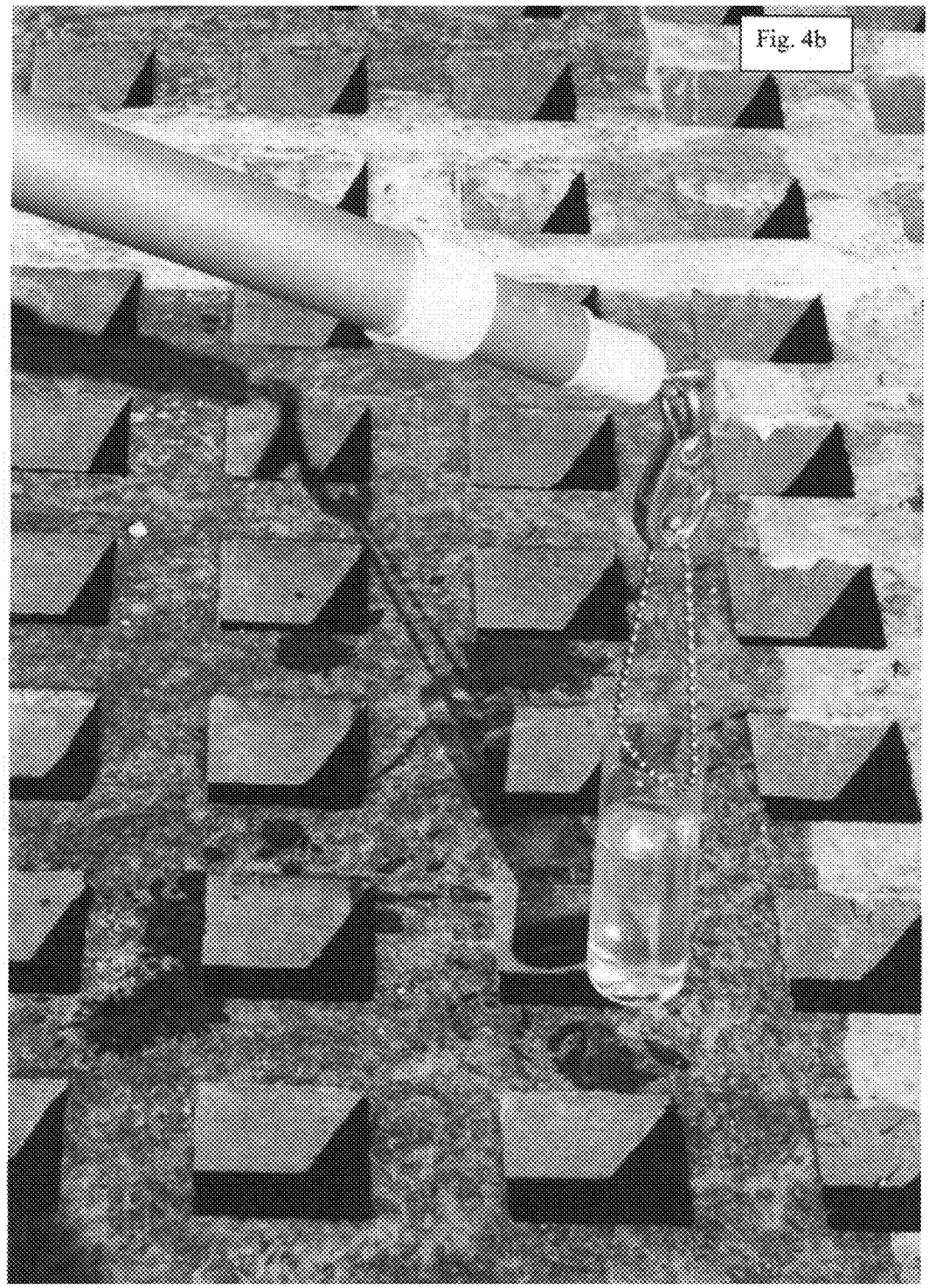

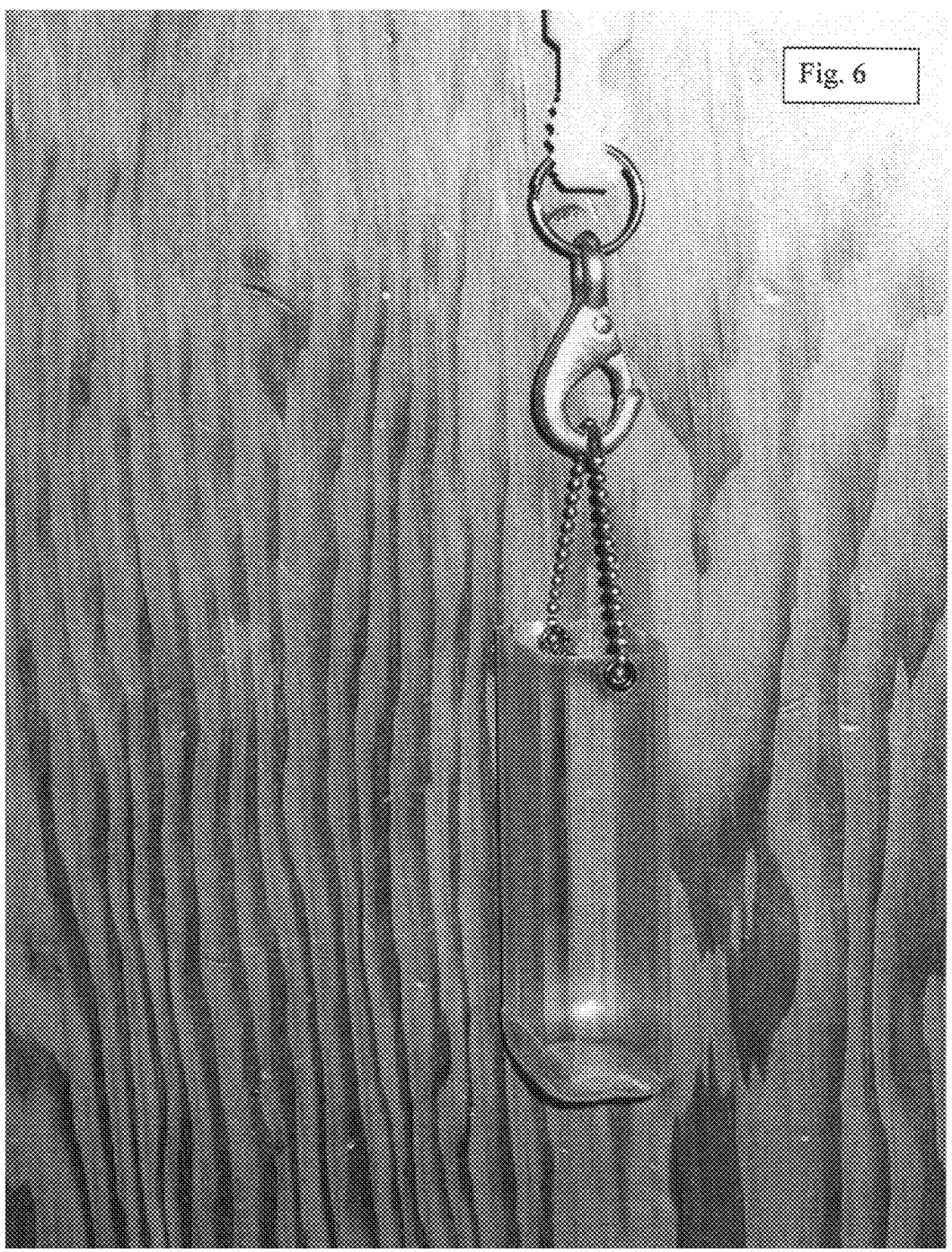

SAMPLE COLLECTION ARRANGEMENT OPERATIVE IN ENVIRONMENTS OF RESTRICTED ACCESS

PRIOR FILING

"Applicant claims the benefit of Provisional Application Ser. No. 60/361,802, filed Mar. 5, 2002" with the following: This application is a Continuation of Application Ser. No. 10/379,348, filed Mar. 4, 2003, now abandoned which claims the benefit of Provisional Application Ser. No. 60/361,802, filed Mar. 5, 2002.

BACKGROUND OF THE INVENTION

Discovery of the West Nile Virus in the tri-state metropolitan area in 1999, and more particularly the resulting concerns of public health officials over the possibilities of the spread of such disease regionally, together with its life-threatening capability, spurred a broad resurgence in the study, surveillance and control of the populations of disease-carrying insects in the Northeast United States, especially mosquitoes. The World Trade Center tragedy served to heightened concerns in such geographical area, particularly when viewed in the light of one West Nile theory that introduction of such disease into the greater New York area may not have been accidental or naturally caused.

Historically, the "front line" of mosquito surveillance, and therefore control, has principally taken the form of fieldwork, in which all four metamorphic forms of the mosquito (i.e., egg, larvae & pupa [all waterborne] and adult [airborne]) are observed and collected/captured. Of these, surveillance and treatment/control primarily are concerned with the larval and adult forms. The former is highly practical, inasmuch as mosquito larvae are almost exclusively found in standing water, and yet are mobile and thus readily subject to collection via the taking of random water samples, particularly inasmuch as they must come to the surface of the water to breath. The adult forms of mosquito are typically gathered in traps designed for flying insects, and therefrom researchers can learn inter alia of the types of species, their range and migration patterns and many other facts about these potentially dangerous airborne pests.

Whereas, the traps for capturing adult mosquitoes are most often installed/implemented on dry land in readily accessible locations, this, unfortunately, cannot be said in many cases with regard to studies, surveillance and treatment/control concerning mosquito larvae, because standing water often is located in remote places and/or in situations that pose great difficulty in terms of physical accessibility. In fact the researcher or field operative has to contend with a very broad range of breeding habitats both natural, e.g., tree holes and hollowed trunks, swampy areas, etc., and man made, such as partially filled swimming pools, sewer treatment plant ponds, and "junk yard" articles such as rimless automobile tires. It is an often overlooked point, too, that determination of the absence of targeted pests is as important as their presence, in terms of integrated pest management, particularly since the presence or absence of targeted pests constitutes the first crucial step in determining whether control measures are to be brought to bear or not.

A most typical and perplexing example of environmental concern the researcher or field operative faces is the man-made culvert or catch basin. These devices are usually located along our roads, where they typically have curb openings, but they also may be employed as a solution for flood control and/or off-road rainwater accumulation, and can, therefore, be found in fields (such as football or soccer fields) and other areas away/remote from our roadbeds, with no openings other than the orifices found in the heavy metal grates forming the only exposed part thereof.

Sampling of the various standing water sources typically takes the form of obtaining or collecting a water sample, and there transferring the sample to a container for transport to lab facilities. The objective, of course, is to capture in the samples taken a number of the mosquito larvae present in that source of water. Accordingly, the larger the sample the greater the likelihood of obtaining an appreciable number of larvae, and the less attempts at collection required to obtain the desired full sample volume.

Of the considerable number of challenges facing the field researcher/operative, catch basins and culverts present a particularly perplexing problem, primarily because of the very restricted access to the water source presented by the physical structure of the environment defining such "sources" of standing water, or at least access thereto. In most cases, the only practical means of access to the water in a catch basin is through its very heavy, "perforated" metal grate, for it is most often the case that no practical means are available to the field personnel to lift the grates and reset them when done, especially when the basin is located well "off-road". Such an exercise would also be very time consuming and potentially harmful to the field personnel and others if not properly and carefully undertaken. Adding to the difficulties field personnel typically face is the fact that the surface of the water can easily be as much as six to eight (or more) feet below the grate, and at times is not situated directly below the grate. Thus, even with a curb opening, the standing water in the typical road catch basin is most often not readily accessible, in that with current devices, field personnel are forced to assume a prone position in attempting to reach the water, which can be dangerous from the standpoints of traffic and the heat of the pavement and metal grate.

Whereas, a mosquito might consider the holes or openings in the grates equivalent to super highways in terms of inconsequential impediment to their passage in and out of the standing water in a catch basin, field personnel are faced with the task of trying to obtain a sizable larvae-populated water sample, in a single attempt, potentially 6-8 (or more) feet below grate level, often blindly, and at significant angle with respect to the plane of the grate, solely through the highly restricting holes or openings in the grate. Studies of various catch basin grates reveal the openings are typically somewhat elongated and either substantially rectangular or oval/oblong in shape (though occasionally the openings are found to be substantially square), with the dimensions of the standard holes being as little as an inch (square or in cross-sectional dimension), and as little as approximately 2½ inches in longitudinal dimension for the elongated openings. What is most important is the fact that field researchers cannot realistically avoid having to deal with the aforementioned extremely limiting conditions regarding physical access in such environments.

Actual conditions typically encountered have the added complexity that the subject water source contains various kinds of debris, both man-made and natural. This adds measurably to the difficulties in collecting the water samples, given that such debris usually requires some circumnavigation, which in turn requires added flexibility of operation as directed or controlled from the distal or remote end of one's means of sample collection.

Because of the physical factors involved with catch basins, including the water surface being several feet below the grate, the gathering of water samples with an industry standard dipper (i.e., a twelve fluid ounce hard plastic cup at the end of a fixed-length [e.g., typically 3 feet] dowel or other handle) under such conditions frequently requires the field researcher to lie prostrate on his or her stomach in an attempt to simply reach the water for sampling, through the curb opening if/when there is one. Because there is no uniformity regarding the depth of culverts and catch basins (nor indeed the dimensions of the grate's holes), one can readily encounter instances where the standing water is well out of reach to the standard "dipper" arrangement. Also, in those cases where much if not substantially all the water is located other than directly below the grate, the dimensions of the grate holes tend to severely limit or curtail the angle at which one can utilize the accessing means of any appreciable length, such as a pole, to reach "off-line" standing water sources.

The use of pump-and-hose mechanisms presents its own set of problems beyond what the limiting environment provides. A pump-hose arrangement typically has problems in directivity as to the operative or suction end of the typical hose, and is prone to clogging with regard to debris present in the water source. Electrical pumps are all too often not feasible in fieldwork. Battery-powered arrangements would provide a decidedly cumbersome apparatus to be carting around the terrain, and would likely have inadequate operational duration. Even a hand pump would prove largely impractical, in that the entire apparatus may require more than one operator and its use would tend to be overly time-consuming as well. Moreover, a pump arrangement might prove detrimental/destructive to the organisms sought to be surveilled.

The prior art, beginning with the standard dipper currently employed, as embodied in U.S. Pat. No. 4,061,038 ("038"), possesses one or more of the aforementioned shortcomings, and/or otherwise falls short of an ability to adequately deal with conditions the field operator is forced to contend with, particularly the highly restrictive catch basin and other limited-access environments the field operator must typically encounter.

Regarding the current standing-water sampling device depicted in the "038" reference, there is provided a pole-like handle, which, though of fixed (i.e., non-telescoping or otherwise extendable) length, can perhaps be presumed to vary from embodiment to embodiment. The operative end is a cup, with lips defining opposing pouring grooves. In transferring the collected sample to a transport container, the entire device must be turned substantially upside down to successfully complete transfer.

U.S. Pat. No. 5,442,970 ("970") depicts a water-sampling device, having a telescopic pole, with the sample container attached to the one end of the pole. The sample container is demountably coupled to the pole not unlike the typical "snap-on" arrangement(s) employed in connection with swimming pool tools (such as a cleaning brush), though a $2^{nd}$ embodiment shows the container could be attachable to the pole via a threaded mounting arrangement. The sample container is, however, taught to be substantially rigidly mounted to the pole, and, thus, like the aforementioned standard dipper, must be substantially turned upside down to effect transfer of the sample to the transport container. Moreover, there appears no solution in the "970" teachings for use in connection with highly restrictive or virtually inaccessible bodies of standing water, such as fully grated catch basins with small apertures. There appears to be some suggestion in the "970" reference, however, that sample containers of varying size can be utilized. Notwithstanding, the device of the "970" patent, as is the case with the above-mentioned prior art arrangements, is deemed unable to suggest any means at the operative end that is loosely or flexibly mountable. The "970" reference also fails to teach any implement being connected to the "handle" or distal end of the pole, such as other sample containers, or a securing/extending (extension) cord.

U.S. Pat. No. 5,601,324 ("324") deals with a means of coupling a liquid sampling container relative to the pole or handle on other than a fixed basis. What is described is a rather elaborate clamping arrangement that encircles the container, whereby the container's diameter is effectively and disadvantageously enlarged considerably. This would tend to render the arrangement ineffective with regard to typical highly restrictive field environments herein contemplated. One portion of the clamping arrangement has a pivot that is attached to the pole. Thereby, the container's opening may be movable relative to the pole in a limited up-and-down arc, i.e., essentially in a single reversible angular direction. The arrangement also does not appear to allow the sample cup to remain upright when bringing the sample toward the inspector in the collection process and/or when transferring the sample to the collection/transport container. Thus, while some limited flexibility appears provided in connection with coupling the container to the pole, there is provided insufficient freedom of movement of the container relative to the pole needed for the operations and environments described. Overall, the complexity and unwieldiness of the pivoted clamping mechanism is unnecessary for, and would hinder, sampling under conditions the present invention was designed to overcome. In addition, securing the container to and releasing the container from the clamping means would require articulate hand movements that would make use largely intolerable in the field, e.g., time lost, polluted water, wearing gloves, etc.

Other arrangements are known to the prior art. However, as to those other arrangements and references for which specific awareness exists, none is deemed to advance the position of the prior art materially closer to the present invention.

U.S. Pat. No. 6,293,601 ("601") teaches an extendable, i.e., telescoping, pole with a hook arrangement at the operative end and a resilient clip type arrangement at the handle end for attachment of the device to a pocket flap. U.S. Pat. No. 4,659,125 describes a telescopic pole having at its operative end a golf ball retriever/receptacle. U.S. Pat. No. 3,960,021 depicts a rod, curved into a handle at one end, and an annular collar fixed to the rod near the other end, for holding a container. This arrangement does not, however, appear to allow for skimming the body of water due to poor maneuverability with limited access constraint(s). Near the end of the handle is a means for removing/replacing the container cap without touching the cap, for sanitary purposes. U.S. Pat. No. 4,754,656 shows an elongated fixed (rather short) handle, to which is attached a cap, in breakaway fashion, with the cap in turn being "hinged" to the container via a plastic hinge. U.S. Pat. No. 5,902,940 illustrates an elaborate tubular sampling arrangement and container, for sampling in narrow wells or borings. U.S. Pat. No. 4,869,118 depicts an elaborate sampling arrangement having an elongated fixed pole/pipe through which there extends longitudinally a control shaft having a handle at the one end and a stopper at the other end. To the stopper end of the pole there is attached a container holder which places the container such that the stopper can be inserted into the opening of the container and retrieved to an "open-container" position via the remote handle. This arrangement appears to have been designed to sample at predetermined depth, and does not appear to allow for tipping of the container to e.g., collect in shallow water. Larval collection requires skimming the surface, as well as dunking for the organisms that have "gone to the bottom" after the water's surface was disturbed.

SUMMARY OF THE INVENTION

Thus, the principal objective of the present invention is to provide an arrangement that would be fully and adequately functional in the environments and environmental conditions contemplated, while avoiding the drawbacks presented by the prior art.

According to the present invention, there is provided an arrangement for obtaining an organism-populated sample of predetermined volume from a liquid source present in an environment of potentially highly restricted physical access, which comprises a first container means for receiving at least a substantial portion of the sample, the container means being sized to accommodate the encountered environment while possessing a capacity enabling collection of the predetermined volume of liquid from a minimal number of collection attempts, and the container means has an opening for communicating with the liquid source; pole means having proximal and distal ends extendable relative to one another, the pole means being structured to accommodate the encountered environment over a predetermined range of extension to enable sample collection remotely relative to the environment; and means for coupling the container means to the pole means at least proximate one end thereof, the coupling means being structured to enable the opening of the container means to be flexibly oriented in relation to the liquid source through virtually any acute angle relative to the longitudinal dimension of the pole means, approaching a spherical range of angles relative to such longitudinal dimension, that is particularly advantageous not only in the sample collection process per se but in the transfer of the sample to the transport container.

Further according to the invention, there is provided an arrangement for collecting and retrieving one or more organism-populated samples of relatively substantial volume from a remotely-located liquid of highly restricted physical access, wherein virtually the entire operative part of the arrangement is capable of permeating or projecting into and through a wide variety of encounterable environments, which comprises a telescoping pole means capable of longitudinal extension from a minimized transport and/or storage mode within a range sufficient to operatively accommodate such environments, while being able to be "locked" into any of such positions of storage, transport and use, the pole means having a substantially uniform cross-section which is sufficiently minimized for operatively negotiating the highly limiting environmental conditions restricting access to the liquid, through a substantial range of acute operative angles relative to any encountered plane of the environment and/or the subject water source, liquid collection container means coupled to the pole means proximate one end thereof for orientation at virtually any acute angle relative to the axis of the pole, constructed of a material that permits observation of its content both within and without the immediate sampling environment, the container means being shaped and sized to be operative in virtually any highly physically restrictive environment while providing an obtainable volume commensurate with the amount of liquid desired in a resultant sample as taken over a predetermined desirable minimum number of samplings, the container having an opening on at least one side or end surface so as to have an orientation in which the opening is normally associated with an upper portion or surface of the container relative to the subject body of liquid prior to and/or during immersion, and means for flexibly and demountably coupling the container means to the pole means, while providing physical properties sufficient to enable partial directivity of the container means relative to the source of the liquid to be sampled, the coupling means, container means and pole means all being constructed of environmentally resistant (e.g., non-corroding) material.

To allow for greater flexibility of operation, a second (or additional) collection container means may be demountably coupled to what is termed herein the distal end (i.e., the non-operating end) of the pole means. In this way, a second (or greater number of) container means, preferably of differing size(s), shapes and/or volumes, particularly with respect to the container means already mounted to the proximal end of the pole means, may be stored on the apparatus itself, as alternate(s) to said already mounted container means. This affords the field operator additional flexibility with regard to the varying restrictive environmental conditions encountered, such as the grate holes of catch basins having no curb opening, and instances where access may not necessarily be the major concern but the shallowness of a "drying-down" water source is.

In a first principal embodiment, the aforesaid coupling means may incorporate the following. The end of the pole means may be provided with threading, either interiorly in a recess or exteriorly. The means by which the collection container means may be coupled to either end of the pole means can therefore include means taking the form of a suitably threaded cap or plug (corresponding to the exteriorly or interiorly threaded pole ends respectively). Alternatively, the coupling means may be connectable to the pole means by a so-called snap-in arrangement as is well known to the connection art. In either case, the container means are readily interchangeable, and thus the field operator may have with him or her a set of two or more container means, of varying shape and/or volume/capacity which can be readily mounted or coupled to the pole means.

In perhaps a simplest form, the container means could be flexibly connected to the pole means, through use of the above-described portion of the coupling means, by at least one sturdy strand of string, thin wire or rope, ball chain, small link chain, plastic lace, and the like. In a preferred embodiment, the strand is secured to the container means proximate a first appropriate upper location relative to the operative opening therein, and extends a predetermined distance to the threaded coupler and returns to be secured to the container means proximate a second location substantially opposite the first securing location. Alternatively the ends of the strand may pass through the wall and into the interior of the container means, to be there secured to each other, thereby forming a continuous loop, for added strength and security.

In all cases, the portion of the coupling means engaging the container means does not increase or otherwise adversely affect or impact any dimension of the container means nor the latter's ability to accommodate and pass through the encountered environment to reach the liquid source to be sampled. Notwithstanding, the coupling means is structured to enable the pole means and/or the coupling means to provide at least partial directivity of the container means relative to the liquid source, to facilitate sample collection.

For operational security reasons primarily, means may be provided proximate the distal end of the pole means (again, the so-called non-operating end of the pole means, i.e., the end opposite to that being utilized to obtain a sample), by which one can connect a rope or similar means, with the other end thereof connected to the operator by any suitable means known to the art, such as a clip or wrist loop. This feature effectively extends the longitudinal reach of operation beyond the predetermined extension limit of the pole while preventing separation from the operator beyond a predetermined distance constituting the preponderance of such reach extension. In this way, the operator is assured the entire device will not be lost by accident, for example, in a deep basin, while allowing access with regard to depths exceeding the fully extended pole, e.g., depths up to twelve (12) feet, which are not all that uncommon.

With regard to the collection container per se, preferably it is constructed of environmentally resistant (e.g., non-corroding), light-weight, substantially transparent material, such as a suitable plastic, non-breakable glass, Plexiglas or acrylic, and preferably would be substantially transparent for ease of spotting/viewing the presence of larvae in the sample taken, through the wall of the container. The ability to spot the presence of larvae in the sample being drawn may be measurably enhanced by securing a white (or near-white or other light colored) waterproof label to one side or a portion of the side of the collection container (either inner or outer surface). Preferably, the container itself can be rendered opaque on a portion of its interior or exterior surface, such that a light-colored background is provided for ease of viewing the container contents.

In terms of volume, while the cross-section of the container would have to adhere to the environmental limitations, for example, those posed by the small openings in the catch basin grates, the container could be somewhat tubular shaped or elongated, while providing a conforming or accommodatable cross-section, for purposes of increasing the volume of each sample taken on a single operation of collection, thus reducing the number of operations or collection attempts needed to be taken to complete a typical quart-sized sample transport container. In this way, appropriately shaped containers in the range of up to twelve fluid ounces (12 oz.) prove quite suitable without becoming unwieldy within the restrictive environment encountered.

The coupling employed in connection with a second (or third) container, herein primarily considered associated with the distal end of the pole means, can but is not required to be structured in essentially the same manner as that employed with the first container means, as described heretofore in connection with the so-called operative or proximal end of the pole means, thus having a container means simultaneously coupled to each end of the pole means, rendering both ends of the pole means potentially fully operative. With the respective containers being of different size/volume and/or different shape, the operator is provided a choice of designating as the operative or proximal end that which has associated therewith the container means most conducive to the restrictions comprising the encountered environment. In instances of environmental encounters conducive to use of the alternate end of the apparatus, one might wish to remove the security rope to avoid its immersion in the liquid source or entanglement in the encountered environment.

The sturdy yet highly flexible strand forming a part of the coupling means between the pole means and the container means, engages the container means at or proximate a first appropriate upper location relative to the operative opening therein, and extends the predetermined distance (typically on the order of three inches) to the portion of the coupling means that engages the pole means, and returns to again engage the container means at or proximate an opposing second location. Preferably, the ends of the strand pass through the wall and into the interior of the container means, to there engage each other, thereby forming a substantially continuous loop, for added strength and security. Alternatively, the strand provided may be a continuous loop of material.

BRIEF DESCRIPTION OF THE DRAWINGS

The above-mentioned and other objectives, features, attributes and advantages of the present invention will become more apparent, and the invention itself better understood, from the following detailed description, taken in conjunction with the accompanying drawings/figures, as to which:

FIG. 1 is a perspective view of a complete first preferred embodiment of the apparatus;

FIGS. 2A and 2B are close-up views of an operating or proximal end of the apparatus, and illustrating in particular alternative approaches to the container means and to the proximal end of the pole means per se;

FIGS. 3A and 3B are close-up views of a distal end of the apparatus, illustrating alternative approaches to the container means and the security means;

FIGS. 4A and 4B depict respectively an operator utilizing the apparatus in a typical catch basin environment and a close-up view of the operative end of the apparatus, illustrating a collected water sample from such environment;

FIG. 5 shows an operator utilizing the apparatus in a fully grated catch basin environment, using the security rope as an extension for the deep basin encountered;

FIG. 6 illustrates in another close-up view of the operative end of the pole means, variants in container shape and other properties as well as an alternative approach to the end of the pole means per se.

DETAILED DESCRIPTION

Figure 2A:
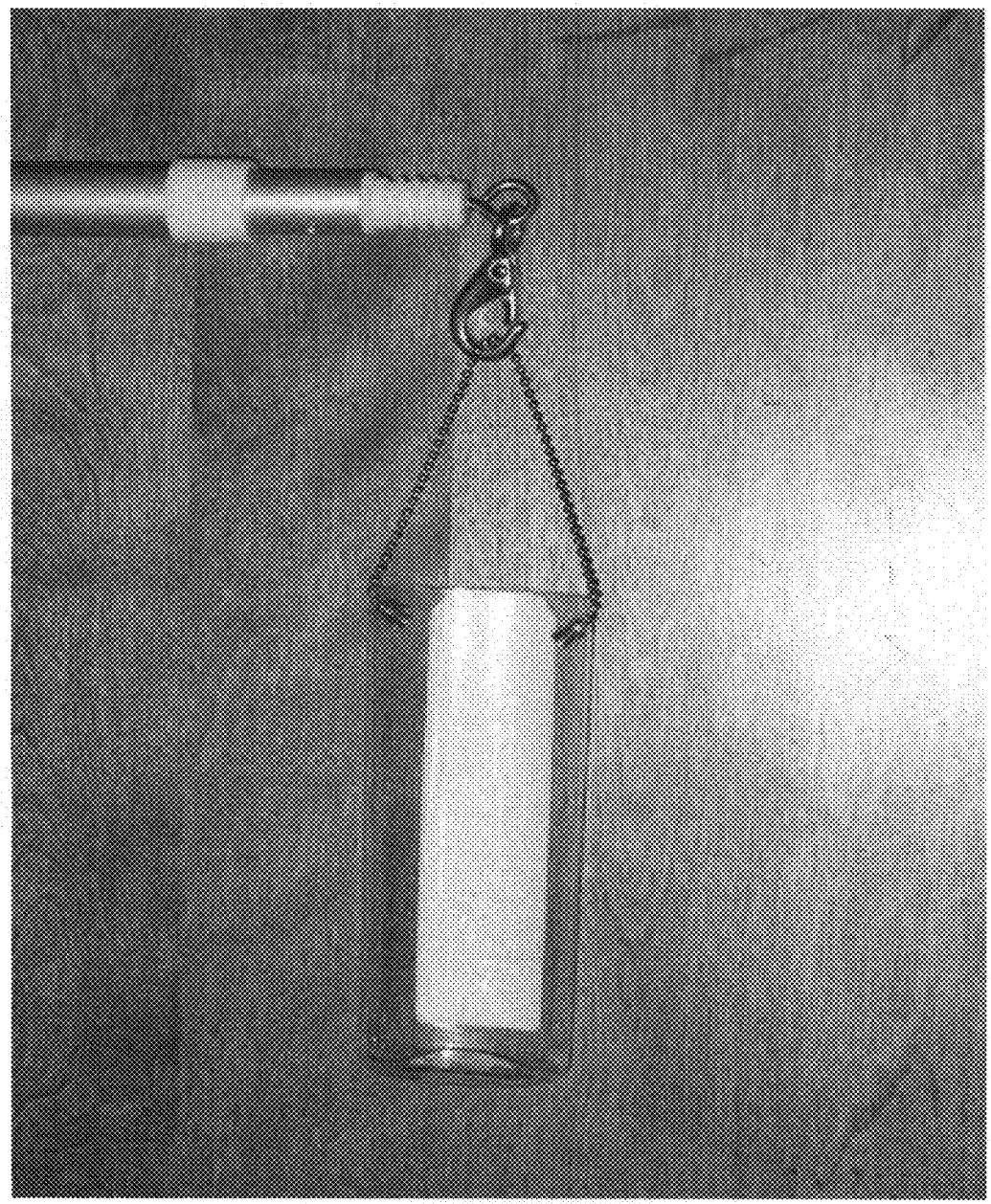

FIG. 1 depicts the full apparatus in a non-operated state, for purposes of illustration. The central portion of the arrangement constitutes a telescoping pole 1, of the type well known in the art, which has been adjusted to approach its smallest longitudinal dimension, typically around four feet (though commercially available assemblies include e.g., pole lengths of three feet [extendable to approximately six feet], five feet [extendable to approximately ten feet] and six feet [extendable to approximately twelve feet]). When fully extended, such typical telescopic arrangement could yield a total longitudinal dimension on the order of eight feet. The operative end 1a (herein also referred-to as the proximate end) of the pole 1 has coupled thereto a collection container 2 of desired type, shape and volume/size. The container 2 is connected to the operative end 1a of the pole 1 via a coupling arrangement 3.

The other end 1b of the pole 1 is herein referred-to as the non-operative or distal end of the pole. In FIG. 1, a rope or cord arrangement 4 is shown in association with the distal end 1b of the pole. The rope 4 is connected to the pole 1 by a second coupling means 5. The second coupling means may take substantially the same form as coupling means 3. However, in FIG. 1, the second coupling means is shown to comprise a metallic loop integral with the distal end 1b per se and a safety clip such as a carabineer. The primary purpose of the rope arrangement is to prevent the accidental loss of the entire apparatus in for example an environment having a depth dimension (the water and/or the space above it) that potentially exceeds the length of the apparatus as fully extended, together with providing a means of extension for sampling in deep basins.

Also depicted as being associated with the distal end 1b is a second container 6, which, like the first container 2, is substantially transparent and possessing an opening at or proximate one end thereof, the end intended to be closest to the pole when operated. The second container 6 is preferably sized or shaped differently relative to the first container 2, thereby providing the operator with a set of at least two containers useful in addressing different environments encountered, such as catch basins having different aperture dimensions, particularly as to their most limiting or restricting dimension, and/or different water depths (e.g., very shallow water generally requiring employment of a small container). In its principal intended mode of operation, the second container is essentially stored on the apparatus per se at the distal end, and may be exchanged with the first container at the proximate end. Alternatively, the operator could use either end of the apparatus, and accordingly engaging the container most conducive to the environmental limitations.

The pole is constructed of a durable, minimally flexible lightweight material that will resist corroding and rusting, such as a suitable plastic or metal, e.g., aluminum. Indeed, the entire apparatus, including all coupling means and the containers, is constructed of lightweight materials that are able to resist corrosion and other adverse affects of the natural elements and environment.

FIGS. 2A and 2B depict the proximal or operative end 1a of the arrangement. In both cases, a fixed-position or rigid loop 10, such as an eyehook, typically brass or stainless steel or other non-corroding/rusting material, is fastened (e.g., screwed) to the end 1a of the telescopic pole 1. A similarly non-corroding/rust-resistant hook-shaped safety clip 11 is secured to the eyehook 10 in such a way as to provide maximal flexibility of movement and positioning of the safety clip 11 relative to the eyehook 10, while nevertheless being well secured thereto. The piece 11 could alternatively take other suitable form, such as a substantially circular stainless steel ring (similar to those employable in connection with ring binders) or a standard carabineer.

The safety clip 11 in turn possesses the means to demountably yet lockingly engage the portion of the coupling means 12 that connects to the container 2. In this way engagement of the container means to the pole means is facilitated while ensuring the container will not be accidentally lost in operation. The weight of the safety clip 11 may advantageously be employed to assist in the collection of the liquid sample by allowing the clip to physically contact the container 2 to facilitate its immersion in the liquid source (as opposed to it substantially floating on the surface). The end 1a of the pole means may also be brought to bear to ease the container into an immersion state. The depicted connecting means between the hook-shaped safety clip 11 and the container 2 is a single piece of ball chain 12 with the typical ball chain connectors 13 occupying either end of the ball chain 12. Though a ball chain embodiment is shown and preferable, this portion 12 of the coupling means 3 (and 5 in FIG. 3) can be instead a strong string, cord, plastic lace, very thin highly flexible wire, small-link chain, and any other suitable (strong and durable) strand of material having relevant physical properties similar to a ball chain.

In the embodiment of FIG. 2a, the connecting ends 13 of the ball chain 12 are allowed to be disconnected or otherwise apart from one another. The ball chain 12 passes though holes or orifices in the side of the container 2 (not particularly shown in FIG. 2), the essential (e.g., diameter) dimension of which readily allows passage the ball chain strand per se through the holes but prevents passage of the connecting means 13. The aforementioned holes in the container are arranged substantially opposite one another. In the embodiment of FIG. 2b, the container 2 is coupled to the pole by the coupling means, whereby the ball chain forms a substantially continuous loop via, e.g., a single ball chain connector 13a (or multiple employment thereof as actually shown in FIG. 2b, thus providing additional security to the arrangement.

The flexibility of the container means suspension as provided by the coupling means according to the invention, readily enables sampling under virtually all kinds of conditions while allowing the collected sample to remain in the container when it is brought to the surface of the liquid and brought through the highly restricting environment encountered. Further, this flexible coupling means arrangement facilitates ease of transferring the collected sample to the transport container, without having to make articulate or complicated movements of the pole means in effecting the sample's transfer (e.g., having to turn the entire apparatus substantially upside down where the container is fixedly connected to the pole means or is only marginally movable relative to the pole means).

As shown in FIGS. 2a and 2b, the collection container 2 is preferably made of a clear or substantially clear, lightweight, plastic or acrylic material, though the container could also be break-resistant glass or Plexiglas. The container is shaped/sized to accommodate the most restrictive of encounterable physical environments, e.g., the holes or openings in the grates of catch basins. In the depicted case, FIGS. 2a & 2b illustrate a somewhat flattened tubular shaped container, i.e., an oblong or oval cross-section. The particular container depicted is capable of holding a volume of liquid on the order of twelve fluid ounces.

In FIG. 2a, one side of the clear container 2 is provided with a substantially white waterproof "backing" material 14, to enhance viewability. The background-enhancing material 14 may be applied to either the interior or exterior of the container. Alternatively a broad portion (e.g., the side) of the elongated container may be treated (e.g., rendered opaque) so as to itself provide a contrasting surface for augmenting viewability of the container contents.

In another embodiment, though not specifically shown, a cylindrically shaped (e.g., FIG. 5) container 2 as small as one inch in diameter and in excess of seven inches in length/height constitutes a fully workable configuration in the most physically restrictive environments known or encountered, while providing a sample volume on the order of three fluid ounces. Shorter versions of such configuration would allow for ease of operation in connection with catch basin water that is very shallow (i.e., is drying out).

In FIGS. 2a and 2b, the container 2 is shown flexibly secured to the coupling arrangement via a preferred arrangement comprising a single ball chain strand, whereby the container opening substantially faces, i.e., is closest to, the pole 1. In the embodiments depicted in FIGS. 2a and 2b, the opening 15 is dimensioned to represent virtually the entire one end of the container. In both FIGS. 2a and 2b, which depict the full course of the ball chain, the holes or apertures through which the two ends of the ball chain run through the side surface(s) of the container, are located not only substantially opposite one another, but are also proximate the open end or orifice 15 of the container 2. Preferably the container will have a single opening or orifice 15 via which the sample is intended to enter the container 2 during sampling.

Figure 3A:
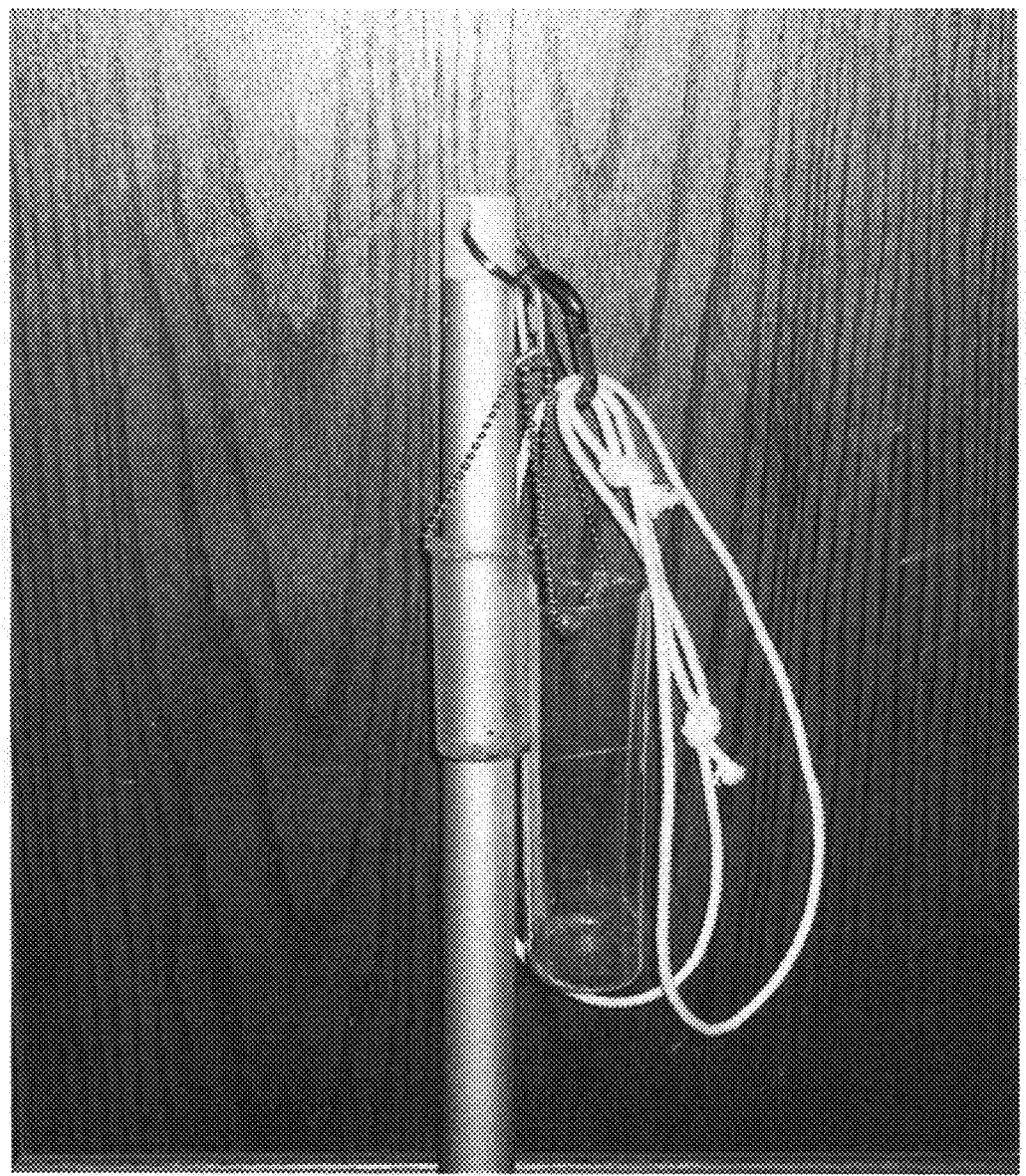

FIGS. 3a and 3b depict, in close-up views, what is herein referred-to as the distal end 1b of the pole 1, with its own coupling means 5. In the particular arrangements shown, the end portion 1b of the pole 1 is provided with a loop 5a. Aside from providing a convenient means for storing the apparatus by hanging it, the loop 5a advantageously enables one or more alternate containers 6a, 6b and a security rope 4, 4a to be secured to the distal end 1b by any suitable means. In the example(s) of embodiment shown, the pair of alternate containers 6a, 6b and the security rope or cord 4,4b are securely associated with the pole 1 by a standard safety clip 5b. Notwithstanding, as mentioned hereinbefore, at least one of the alternate container(s) 6a, 6b could be secured to the distal end 1b of the pole 1 in substantially the same fashion as the container 2 is secured to the proximal or operative end 1a of the pole. In this way both ends of the pole 1 are rendered fully operative, and thus provide the operator with augmented and time-saving flexibility in his or her selection between different sized/shaped/volumed containers already mounted to the pole, thereby increasing the arrangement's adaptability in going from environment to environment of varying restrictive access.

Though not particularly shown in FIGS. 3a and 3b, the loop 5a at the alternate end 1b of the pole, and the eye-hook 10 at the primary end 1a of the pole, could instead be, or be part of, the within-described threaded plug or cap integrally structured to provide the appropriate loop, wherein the threading suitably engages threading associated with the respective end of the pole or a recess in the end of the pole (or may alternatively take the integrally structured form depicted in FIGS. 2b and 6). In this way, ease of interchangeability of the containers, including yet a third (or more) containers of a full container set, is assured. Thus, the apparatus can be facilitated via a kit of multiple containers each of preferred different size/shape/volume.

FIG. 3b illustrates, apart from FIG. 3a, several additional attributes of the present. The alternate container 6b is provided with a volume marking (in this case two fluid ounces) on the side. Security rope 4a is the so-called plastic lace (craft lanyard type material) or woven nylon rope. Additionally, the distal end 1b of the pole is provided with a plastic hanging arrangement 20 for storing the apparatus when not in use.

Figure 4A:

FIGS. 4a and 4b show respectively a field operator drawing a water sample from and through the grate 31 of a typical catch basin 30, and in close-up view, the operative end of the apparatus, illustrating a collected water sample from such environment. In FIG. 4a, resting on the rim 32 of this particular type of catch basin is shown a quart-size transport container 35 (as well as a large flash light 34). In this situation, the operator has had to extend the telescopic pole 1 enough to enable the collection container 2 to reach the water in the catch basin 30, through one of the grate's holes 33, while remaining in an upright posture. FIG. 4b illustrates the ability to obtain a water sample from the depths of a catch basin 30, despite the grate openings 33 (in this case substantially square and on the order of 1¼ inches in dimension) being so severely physically restrictive. In this case, a container 2, though substantially circular in cross-section, is adaptable to that environment through the judicious selection of appropriate container cross-section.

FIGS. 4a and 4b well illustrate the aspect of different shaped holes 33 in the grates of the catch basins typically encountered by the field operator. As can be seen in FIGS. 4a and 4b, in addition to the collection container 2 being sized to fit through the grate 31 openings 33, the pole 1 is thin enough in cross-section to enable the operator to orient the pole at a substantial range of angles through the grate openings 33. The flexibility of the coupling 3 of the container 2 to the pole 1 enables the operator to readily gather the water sample by having the container traverse as much of the standing body of the water as desired, as situated in this highly physically restrictive environment. This is accomplished through angular reorientation of the pole, without having to be concerned with the orientation of the container's orifice 15. FIG. 5 shows a field operator employing the sampling apparatus in connection with a catch basin 30 where no curb opening exists. In the situation depicted, the operator is forced to contend with a deep basin, such that the entire pole 1 except for the distal end 1b is required, even in the fully extended mode, to reach the standing water captured in the basin. Grate 31 is here shown to possess small-dimensioned substantially square apertures 33, and the operator has made her selection of container means accordingly. FIG. 5 well illustrates the use and advantages of the security rope 4, wherein the end secured to the operator is in the form of a wrist loop, and the other end of the security rope is coupled to the distal end 1b of the pole via safety clip 5b, typically as described herein.

FIG. 6 illustrates, in yet another close-up view of the operative end 1a of the pole means 1, multiple additional features of the apparatus according to the invention. In this instance, the operative end 1a of the pole is comprised of an entirely plastic end piece, with a loop 22 that replaces the need for an eye-hook. This particular end mechanism of the pole is also shown in FIG. 2b. coupling means is completed in this embodiment by a stainless steel (or equivalent) ring, similar to those employed in ring binders, which couples the pole 1 to the safety clip 11.

The container 2 of FIG. 6 advantageously employs reinforced holes 21, through which the ball chain 12 passes. Reinforcement make take any suitable environmentally resistant form, such as hard plastic or Teflon eyelets (the latter particularly facilitating movement of the ball chain, or other employed version 12 of the coupling means, advantageously with respect to the container. The element of reinforced holes 21 in the container(s) ensures against wear and tear and breakdown of the container means over prolonged use. The particular container 2 depicted in FIG. 6 has its opening comprising the entire top portion, and has a cross-sectional shape that is substantially rectangular, with the corners concave for additional strength and structural integrity. The dimensions of this preferred container are typically on the order of the following: capacity (volume) of six ounces, and 1 inch by 2¼ or 2½ inches in cross-section, with a measuring mark (not particularly shown, though such concept is illustrated in FIG. 3b).

There has been described herein an inexpensive, durable sample collection arrangement adaptable to enable expeditious collection of samples from sources of liquid located in a wide range of environments many of which are considered to be highly restricted in terms of physical access, where the operator is remotely positioned relative to the highly restrictive environment.

The invention claimed is:

1. An arrangement for obtaining an organism-populated sample of predetermined volume from a liquid source present in an environment at least a portion of which environment constitutes highly restricted physical access, comprising first container means for receiving at least a substantial portion of said organism-populated sample, said container means being sized to be accommodated by said restricted access portion of said environment and having a capacity enabling collection of said predetermined volume from a minimal number of collection attempts, said container means having an opening for communicating with said liquid source;

pole means having proximal and distal ends extendable relative to one another for supporting the container means, said pole means being structured to accommodate said restricted access portion of said environment over a predetermined range of extension to enable sample collection remotely relative to said restricted access portion of said environment;

means for coupling the container means to the pole means at least proximate one end thereof, said coupling means including first means for flexibly orienting during sample collection the opening of said container means with respect to the surface of the liquid source through virtually any acute operative angle relative to the longitudinal dimension of the pole means, and further including at least a second container means demountably coupled proximate to the distal end of the pole means, said first and second container means varying in size and/or volume relative to one another, said first and second container means being coupled proximate to respective ends of said pole means, enabling sample collection associated with either end of the pole means and storage of second container means.

2. A sample collection arrangement according to claim 1, wherein said first orienting means is structured to enable orientation of the opening of the first or second container means through a substantially spherical range of angles relative to the longitudinal dimension of said pole means, for collection and holding of the sample.

3. A sample collection arrangement according to claim 2, wherein said first and second container means is elongated and has a cross-section selected from the class of cylindrical, oval, oblong and rectangular cross-section.

4. A sample collection arrangement according to claim 1, wherein the cross-sectional dimension of the pole means is substantially uniform and minimized to enable accommodation of the pole means by said restricted access portion of said environment through a substantial range of acute operative angles relative to any encountered plane of said restricted access portion of said environment and said liquid source.

5. A sample collection arrangement according to claim 4, wherein said pole means is structured to achieve a non-extended orientation for transport and storage.

6. A sample collection arrangement according to claim 2, wherein said coupling means includes means for facilitating accommodation by said environment of said first or second container means.

7. A sample collection arrangement according to claim 2, wherein said first or second container means is composed of a substantially transparent material from the class of plastic, break-resistant glass and acrylic.

8. A sample collection arrangement according to claim 7, wherein said first or second container means has at least a portion of one surface thereof opaque for facilitating viewing of the collected sample, proximate the liquid source.

9. A sample collection arrangement according to claim 8, wherein said opaque portion may be associated with the interior or the exterior of the first or second container means.

10. An arrangement for obtaining an organism-populated sample of predetermined volume from a liquid source present in an environment of potentially highly restricted physical access, comprising first container means for receiving at least a substantial portion of said sample, said container means being sized to be accommodated by said environment while possessing a capacity enabling collection of said predetermined volume from a minimal number of collection attempts, said container means having an opening for communicating with said liquid source;

pole means having proximal and distal ends extendable relative to one another for supporting the container means, said pole means being structured to accommodate said environment over a predetermined range of extension to enable sample collection remotely relative to said environment;

means for coupling the container means to the pole means at least proximate one end thereof, said coupling means being structured to enable the opening of said container means to be flexibly oriented in relation to the liquid source through virtually any acute operative angle relative to the longitudinal dimension of the pole means; and at least a second container means demountably coupled proximate to the distal end of the pole means, said first and second container means varying in size and/or volume relative to one another, said first and second container means being simultaneously coupled proximate to respective ends of said pole means, enabling sample collection associated with either end of the pole means and storage of second container means.

11. A sample collection arrangement according to claim 10, wherein said pole means has a predetermined extension limit, and further including additional extension means having a predetermined length and flexibly coupled proximate to the distal end of the pole means and demountably connectable to an operator, for extending the longitudinal reach of operation beyond the predetermined extension limit of said pole means while preventing separation from the operator beyond said predetermined length, said predetermined length constituting the preponderance of the longitudinal dimension of said pole means as extended to said predetermined extension limit.

12. A sample collection arrangement according to claim 1, wherein the coupling means associated with each of said first and second container means are substantially structurally the same.

13. A sample collection arrangement according to claim 10, wherein said coupling means, first and second container means and pole means are each constructed of environmentally resistant material.

14. An arrangement for obtaining an organism-populated sample of predetermined volume from a liquid source present in an environment at least a portion of which environment constitutes highly restricted physical access, comprising first and second container means for receiving at least a substantial portion of said organism-populated sample, said first and second container means varying in size and/or volume relative to one another and each being sized to be accommodated by said restricted access portion of said environment and having a capacity enabling collection of said predetermined volume from a minimal number of collection attempts, said first and second container means each having an opening for communicating with said liquid source;

pole means having proximal and distal ends extendable relative to one another, for supporting the first and second container means, said pole means being structured to accommodate said restricted access portion of said environment over a predetermined range of extension to enable sample collection remotely relative to said restricted access portion of said environment; and means for demountably coupling the first and second container means proximate to the proximal and distal ends of the pole means respectively, enabling sample collection associated with either end of the pole means and storage of the other of said first and second container means, said coupling means including first means for flexibly orienting during sample collection the opening of said first or second container means with respect to the surface of the liquid source through virtually any acute operative angle relative to the longitudinal dimension of the pole means, said first orienting means of said coupling means comprising first connecting means for connecting to the pole means and second connecting means for connecting to the first or second container means said first and second connecting means being coupled to one another, and said second connecting means comprising at least one strand from the class of durable lace, string, cord, ball chain and link chain, wherein the ends of the strand pass through the wall of the associated container means into the interior thereof, to be there secured to each other, thereby forming a substantially continuous loop.

15. A sample collection arrangement according to claim 14, wherein said second connecting means is comprised of a strand of material secured to the first and second container means proximate a first upper location predeterminably spaced relative to the respective operative opening therein, and extends a predetermined distance to the first connecting means and returns to be secured to the first and second container means proximate a second upper location substantially opposite said first upper location.

16. A sample collection arrangement according the claim 14, wherein said coupling means includes safety clip means for facilitating coupling of the first and second container means to and preventing the first and second container means from becoming accidentally disconnected from the pole means.

17. A sample collection arrangement according the claim 14, wherein said first and second container means includes means for reinforcing engagement thereof with said coupling means, and dimensional indicia associated with at least one surface thereof.

* * * * *